United States Patent [19]

Rodriguez

[11] Patent Number: 4,497,790
[45] Date of Patent: Feb. 5, 1985

[54] METHOD FOR FORMING CATIONIC TECHNETIUM COMPLEXES USEFUL AS RADIODIAGNOSTIC AGENTS

[75] Inventor: Manuel S. Rodriguez, Houston, Tex.

[73] Assignee: E. I. du Pont de Nemours and Company, Inc., Wilmington, Del.

[21] Appl. No.: 414,608

[22] Filed: Sep. 3, 1982

[51] Int. Cl.$^3$ ...................... A61K 43/00; A61K 49/00
[52] U.S. Cl. ................................. 424/1.1; 260/429 R; 260/440; 260/446; 424/9; 568/2; 568/8; 568/13; 568/14; 568/15; 568/16; 568/17
[58] Field of Search .................. 260/429 R, 440, 446; 560/2, 8, 13-17; 424/1.1, 9

[56] References Cited

U.S. PATENT DOCUMENTS

| | | | |
|---|---|---|---|
| 2,587,805 | 3/1952 | Akobjanoff | 260/440 |
| 4,338,248 | 7/1982 | Yokoyama et al. | 424/1.1 |
| 4,363,793 | 12/1982 | Blau et al. | 424/1.1 |
| 4,374,821 | 2/1983 | Glavan et al. | 260/429 R |
| 4,387,087 | 6/1983 | Deutsch et al. | 424/1.1 |
| 4,451,450 | 5/1984 | Subramanyan | 424/1.1 |

FOREIGN PATENT DOCUMENTS 0038756  10/1981  European Pat. Off. ............. 424/1.1

OTHER PUBLICATIONS

Deutsch et al, J. Nucl. Med., 22(10) 897–907 (1981).

Primary Examiner—Christine M. Nucker
Attorney, Agent, or Firm—Sewall P. Bronstein; George W. Neuner

[57] ABSTRACT

The present invention relates to methods for making cationic radiodiagnostic agents and, in particular, to methods for preparing $^{99m}$Tc-labelled cationic radiodiagnostic agents.

14 Claims, No Drawings

METHOD FOR FORMING CATIONIC TECHNETIUM COMPLEXES USEFUL AS RADIODIAGNOSTIC AGENTS

BACKGROUND OF THE INVENTION

Various complexes of monodentate and polydentate ligands with technetium have been made and studied. These complexes generally were made for use in studies to determine the various oxidation states of technetium and for other research regarding the structure of such complexes and metal-coordination chemistry. Such studies have been reported in, for instance, *Chemistry and Industry*, pp. 347-8 (Mar. 26, 1960); *J. Inorg. Nucl. Chem.*, Vol. 28, pp 2293-96 (1966); *Aust. J. Chem.*, 23, pp 453-61 (1970); *Inorganic Chem.*, Vol. 16, No. 5, pp. 1041-48 (1977); *J. Inorg. Nucl. Chem.*, Vol. 39, pp. 1090-92 (1977); and *J. C. S. Dalton*, pp. 125-30 (1976).

Recently, in a presentation to the American Pharmaceutical Association, E. A. Deutsch disclosed that certain complexes of DIARS, i.e.

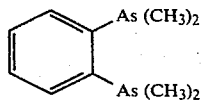

and Tc-99m, and certain complexes of DMPE, i.e. $(CH_3)_2PCH_2CH_2P(CH_3)_2$, and Tc-99m may be useful as radio-diagnostic agents for myocardial or hepatobiliary imaging. $[^{99m}Tc\text{-}(DMPE)_2Cl_2]^+$ and $[^{99m}Tc\text{-}(DIARS)_2Br_2]^{30}$ were prepared by Deutsch by heating in an open flask a reaction mixture containing the appropriate hydrogen halide in aqueous alcohol solution, $^{99m}Tc$-sodium pertechnetate, and ortho-phenylenebis(-dimethylarsine), i.e. DIARS, or bis-(1,2-dimethylphosphino)ethane, i.e. DMPE. The reaction was reported to take about 30 minutes. The labelled complex was then purified by chromatographic methods involving ion exchange columns.

The labelled complex produced according to the procedure of Deutsch has several practical disadvantages. The procedure requires handling several ingredients including an organic solvent to make the reaction mixture and then purifying the resulting radiolabelled complex by chromatography. Each of these handling steps can contaminate the system and final product. The purification step further requires additional time for preparation of the final product. These steps require a skilled technician and are performed at the site of use, just prior to use. Thus, a complex, time consuming chemical preparation is required during which sterility of ingredients and containers is difficult to maintain. Thus, to assure freedom from contamination, a final sterilization step is required, which further adds to preparation time. Because Tc-99m has a short half-life, lengthy preparation methods are undesirable. Thus, the complexity of the preparation, both with regard to maintaining sterile conditions and to purification of the $^{99m}Tc$-labelled complex make the Deutsch procedure undesirable.

It would be highly desirable to have a sterilized kit with all the necessary materials prepared by the manufacturer, to which only the Tc-99m need be added at the site of use to produce the desired labelled complex directly in high enough yield to obviate the need for purification. It would also be desirable for the kit materials to be in a closed container or vial, pre-sterilized, so that the only step to be performed at the site of use would be the addition of the radionuclide. To increase stability and shelf-life of the kit, it would be highly desirable that the materials be readily lyophilized, preferably from an aqueous solution.

By achieving the desirable features outlined above, a convenient-to-use heart imaging radiopharmaceutical agent would be provided that is capable of concentrating in healthy heart tissue to provide a negative image of an infarct, damaged or ischemic tissue.

A copending application, Ser. No. 311,770, filed Oct. 15, 1981 in the name of Vinayakam Subramanyam, which is hereby incorporated by reference, describes an acid salt of a mono or polydentate ligand that is water soluble, stable in a lyophilized state, and is capable of binding with Tc-99m to form a cationic complex. The acid salt may be generally represented by the formula:

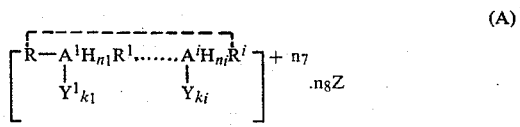

wherein:

i is an integer from 1 to 6;

R, $R^1$, $R^2$, $R^3$, $R^4$, $R^5$ and $R^6$ are each independently selected from hydrogen or substituted or unsubstituted alkyl, aryl, alkylaryl, arylalkyl, monocycloalkyl, polycycloalkyl, heterocyclic and carbocyclic groups, and R plus $R^i$ may be taken together to form a cyclic compound or separately to form a linear compound;

$Y^1$, $Y^2$, $Y^3$, $Y^4$, $Y^5$ and $Y^6$ are independently selected from substituted or unsubstituted alkyl, aryl, alkylaryl, arylalkyl, monocycloalkyl, polyycycloalkyl, heterocyclic and carbocyclic groups;

$A^1$, $A^2$, $A^3$, $A^4$, $A^5$ and $A^6$ are the same or different neutral donor atoms, each having a free-electron pair available for accepting a proton to provide a charged ligand or for complexing with Tc-99m or Tc-99 to form a cationic complex;

Z is preferably a parenterally acceptable anion;

$k_1$, $k_2$, $k_3$, $k_4$, $k_5$ and $k_6$ are each independently zero or one;

$n_1$, $n_2$, $n_3$, $n_4$, $n_5$ and $n_6$ are independently 0 or 1; and $n_7$ and $n_8$ are integers from 1 to 6 where $$n_7 = \sum_{i=1}^{6} n_i$$

and the charge represented by $n_8 Z$ is equal in magnitude and opposite in sign to $+n_7$; or

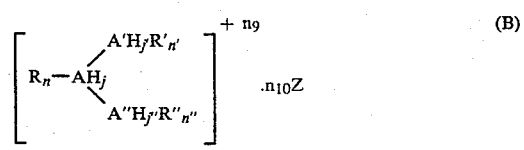

wherein:

R, R′ and R″ are independently selected from hydrogen or substituted or unsubstituted alkyl, aryl, alkylaryl, arylalkyl, monocylcloalkyl, polycycloalkyl, heterocyclic and carbocyclic groups;

A, A′ and A″ are independently selected from the group of neutral donor atoms having a pair of electrons available for accepting a proton to provide a charged ligand or for complexing with Tc-99m or Tc-99 to form a cationic complex;

j, j' and j" are independently 0 or 1;

n, n' and n" are independently the integer 1 or 2;

Z is the same as defined above $n_9$ and $n_{10}$ are integers selected from 1 to about 3, where $n_9 = j + j' + j''$ and the charge represented by $n_{10}Z$ is equal in magnitude and opposite in sign to $+n_9$.

These acid salts are normally solid compounds, water-soluble, readily lyophilized, and capable of reducing pertechnetate and binding with technetium to form stable cationic complexes.

Cationic technetium complexes of these acid salts, useful for radiodiagnostic treatments, are prepared by mixing the acid salt and $^{99m}$Tc-pertechnetate in an aqueous or alcoholic solution and heating the mixture to form the cationic complex. Preferably, the ligand is provided as a lyophilized ligand acid salt as described by V. Subramanyam in copending application Ser. No. 311,770 and is contained in a sealed, sterilized vial prior to adding the pertechnetate. The pertechnetate solution can then be injected into the vial under aseptic conditions to maintain sterility.

However, by following the procedures of Deutsch the yields obtained in the labelling reaction without further purification are generally not sufficient to obtain good images. Therefore, it is desirable to obtain high yields of the cationic technetium complexes for radiodiagnostic uses in one step without the need for purification of the labelled compound.

SUMMARY OF THE INVENTION

The present invention provides a method for making cationic technetium-labelled radiopharmaceutical agents in high yields so that they can be used without the need for purification of the labelled compound. The method of the invention comprises (1) admising $^{99m}$Tc-pertechnetate and a salt of a target-seeking ligand having the structural formula:

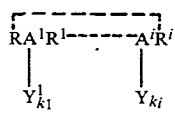

or a water-soluble salt thereof, wherein:

i is an integer from 1 to 6;

R, $R^1$, $R^2$, $R^3$, $R^4$, $R^5$ and $R^6$ are each independently selected from hydrogen or substituted or unsubstituted alkyl, aryl, alkylaryl, arylalkyl, monocycloalkyl, polycycloalkyl, heterocyclic and carbocyclic groups, and R plus $R^i$ may be taken together to form a cyclic compound or separately to form a linear compound;

$Y^1$, $Y^2$, $Y^3$, $Y^4$, $Y^5$ and $Y^6$ are independently selected from hydrogen or substituted or unsubstituted alkyl, aryl, alkylaryl, arylalkyl, monocycloalkyl, polycycloalkyl, heterocyclic and carbocyclic groups;

$A^1$, $A^2$, $A^3$, $A^4$, $A^5$ and $A^6$ are the same or different donor atoms, each having a free-electron pair available for complexing with Tc-99m or Tc-99 to form a cationic complex; and $k_1$, $k_2$, $k_3$, $k_4$, $k_5$ and $k_6$ are each independently zero or one;

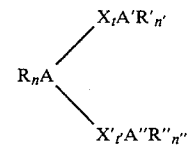

wherein:

R, R' and R" are independently selected from hydrogen or substituted or unsubstituted alkyl, aryl, alkylaryl, arylalkyl, monocycloalkyl, polycycloalkyl, heterocyclic and carbocyclic groups;

X and X' are saturated or unsaturated alkyl groups; A, A' and A" are independently selected from the group of donor atoms having a pair of electrons available for complexing with Tc-99m or Tc-99 to form a cationic complex; t and t' are independently 0 or 1; n is 0, 1 or 2; and n' and n" are independently the integer 1 or 2; or

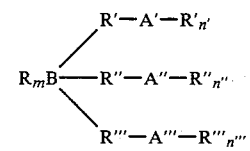

wherein

R, R', R" and R'" are independently selected from hydrogen or substituted or unsubstituted alkyl, aryl, alkylaryl, arylalkyl, monocycloalkyl, polycycloalkyl, heterocyclic and carbocyclic groups;

A', A" and A'" are independently selected from the group of donar atoms having a pair of electrons available for complexing with Tc-99m or Tc-99 to form a cationic complex;

B is an atom selected from the group of donar atoms having a pair of electrons available for complexing with Tc-99m or Tc-99, boron or from the elements listed in Group IV A of the periodic table (i.e. C, Si, Ge, Sn, and Pb);

m is 0 or 1; and n, n', n" and n'" are independently the integer 1 or 2; and (2) heating the admixture to a temperature greater than 100° C. for a suitable length of time to complete the labelling reaction thus forming a technetium-labelled radiopharmaceutical agent.

The R's in formulas I, II and III are preferably substituted or unsubstituted alkyl radicals having 1 to about 6 carbon atoms such as methyl, ethyl, etc., and the like, and substituted or unsubstituted aryl radicals such as benzyl, phenyl, etc., and the like. When more than one R group is attached to the same donor atom, the R groups so attached can be the same or different. Salts of the liquids of formulas I, II and III are preferably water soluble salts such as described by Subramanyam in copending Ser. No. 311,770, as aforesaid.

It is surprising that heating the above admixtures at higher temperatures provides higher yields because heating for longer times at temperatures less than 100° C. does not provide such higher yields. Preferably, the admixture is heated to a temperature between about 130° C. and 150° C., and most preferably the admixture is heated to about 150° C.

The R's in formulas I, II and III are preferably alkyl radicals having 1 to about 6 carbon atoms such as methyl, ethyl, etc., and the like, and aryl radicals such as benzyl, phenyl, etc., and the like.

The cationic complexes formed in accord with this invention are useful for radiodiagnostic tests in connection with myocardial and hepatobiliary tissues.

DETAILED DESCRIPTION OF THE INVENTION

Labelled compositions can be prepared in accord with the present invention from a wide variety of monodentate and polydentate target-seeking ligands. Typical examples of such ligands include, for instance, aryl compounds having arsenic, phosphorus, nitrogen, sulfur, oxygen, selenium, tellurium, or any combination of them, substituted ortho to each other. For example, o-phenylene compounds having the structure:

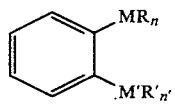
IV in which M and M' are arsenic, phosphorus, nitrogen, sulfur, oxygen, selenium, tellurium, or any combination of them, and n and n' are independently 1 or 2 depending upon the particular donor atom used for M and M', and R and R' are independently hydrogen, or an organic group, preferably an alkyl group having 1 to 6 carbon atoms, an aryl group such as phenyl, or the like, and substituted such groups. When more than one R group is attached to the same donor atom, such R groups can be the same or different. Additional examples of suitable ligands include bidentate tetraethylene ligands of the formula:

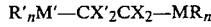
$$R'_nM'—CX'_2CX_2—MR_n \quad V$$

in which M, M', R, and R' are as defined above, n and n' are 1 or 2 depending upon the particular M and M', and X and X' are independently selected from hydrogen, halide, or substituted or unsubstituted lower alkyl groups having 1 to about 6 carbon atoms. Further examples of suitable ligands include those having the formula:

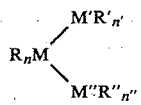

where M, M', R, and R', are as defined above, M" is independently selected from arsenic, phosphorous, nitrogen, sulfur, oxygen, selenium, and tellurium, n is 0 or 1, n' and n" are independently 1 or 2, and R" is independently selected from hydrogen, halide or an organic radical, preferably an alkyl radical having 1 to about 6 carbon atoms, an aryl radical such as phenyl, or the like, and substituted such groups.

Throughout this application, whenever more than one R groups is attached to the same donor atom, such R groups can be the same or different.

Particularly preferred target-seeking ligands for the practice of this invention are the bis-dialkylphosphinoethanes and their substiituted derivatives, including, for example, 1,2-bis(dimethylphosphino)ethane,
1,2-bis(di(trifluouromethyl)phosphino)ethane,
1,2-bis(dimethylphosphino)-1,1-difluoroethane,
1,2-bis(dimethylphosphino)-1-fluoroethane,
1,2bis(dimethylphosphino)propane,
1,2-bis(di(trifluoromethyl)phosphino)-1,1,2,2-tetrafluoroethane,
1,2-bis(di(trifluoromethyl)phosphino)propane,
2,3-bis(di(trifluoromethyl)phosphino)butane,
1,2-bis(di(trifluoromethyl)phosphino)butane,
1,3bis(dimethylphosphino)butane,
1,3-bis(dimethylphosphino)propane,
1,3-bis(di(trifluoromethyl)phosphino)propane,
1,2-bis(dimethylphosphino)-1,1-dichloro-2,2-difluoroethane,
1,2-bis(diethylphosphino)ethane,
1,2-bis(diisopropylphosphino)ethane,
1,2-bis(dipropylphosphino)ethane,
1-dimethylphosphino-2-diisopropylphosphinoethane,
1,2-bis(diisobutylphosphino)ethane
1-dimethylphosphino-2-dimethylarsinoethane, and similar compounds wherein the phosphorus is replaced by nitrogen, arsenic, sulfur, oxygen, selenium tellurium, or any other atom having a free electron pair, and the like.

Other useful target-seeking ligands include the alkylaminobis(difluorophosphine), i.e., $RN(PF_2)_2$, ligands and the like where R is an organic group, preferably an alkyl group having 1 to about 6 carbon atoms, an aryl group as phenyl, or the like, and substituted such groups; and the o-phenylene compounds such as, for example, orthophenylenebis(diarsine), orthophenylenebis(dimethylarsine), orthophenylenebis(diamine), orthophenylenebis(dimethylamine), orthophenylenebis(diphosphine), orthophenylenebis(dimethylphosphine), and the like.

Additional target-seeking ligands suitable for use in the present invention are those described by Nozzo et al., in *J. Amer. Chem. Soc.*, 101, p. 3683 (1979) and by Wilson et al., *J. Amer. Chem. Soc.*, 100, p. 2269 (1978), which are hereby incorporated by reference.

Any donor element can be used in the target-seeking ligand in accord with this invention provided that it is a donor atom having a free-electron pair available for accepting a proton to provide a charged ligand and further provided that it has the capability of complexing with technetium (Tc-99 or Tc-99m) to form a cationic complex in the presence of suitable anions. Suitable such elements include, for instance, phosphorous (P), arsenic (As), nitrogen (N), oxygen (O), sulfur (S), antimony (Sb), selenium (Se), tellurium (Te), and the like. Preferred elements are P and As.

The target-seeking ligands can be provided as the free base or as an acid addition salt thereof as described by V. Subramanyan in copending Ser. No. 311,770.

Labelling in accord with this invention is accomplished by admixing a suitable quantity of $^{99m}$Tc-pertechnetate in solution with a target-seeking ligand, and heating the admixture for suitable length of time at temperature greater than 100° C. Preferably, the admixture is heated to a temperature in the range of about 130° C. to about 150° C., and more preferably to about 150° C. An aqueous physiological saline solution is typically the solution of choice for labelling the target-seeking ligand because it is readily administered to the patient.

As aforesaid, the admixture is heated for a suitable length of time to compelete the labelling reaction. The length of time for reaction is typically in the range of 5 to 30 minutes and preferably less than 30 minutes. However, the time period can vary depending upon the concentration of reactants, the particular target-seeking ligand being labelled, the desired yield of labelled product, the pH of the system, etc. For instance, at a temperature of about 130°–135° C., about 30 minutes of reaction time is typically required, whereas at a temperature of about 150° C., 5 to 10 minutes of reaction time is typically sufficient. The amount of time required to complete reaction can be readily ascertained for any particular set of conditions by those skilled in the art by a few experiments.

It has been found that lyophilized compositions for the preparation of cationic technetium complexes can be improved by the addition of a polyhydroxy-compound to the reaction mixture. The use of the polyhydroxy-compound, for reasons not fully understood, results in a more consistent yield of the cationic technetium complex. Preferred polyhydroxy-compounds, include, for example, Hetastarch (hydroxyethyl starch), mannitol, glycerol, D-mannose, sorbitol, and the like.

To image the heart of a mammal, in-vivo, a radiopharmaceutical preparation made in accord with the invention, having a suitable quantity of radioactivity for the particular mammal, is injected intravenously into the mammal. The mammal is positioned under a scintillation camera in such a way that the heart is covered by the field of view. High quality images of the heart are obtained analogous to those seen in clinical studies using Thallium-201.

In order to obtain high quality images the yield of radioactive labelled cationic technetium complex should preferably a greater than 70% after reconstituting the lyophilized mixture and labelling. Lower yields will result in poorer image quality and undesirable purification steps will be required to produce high quality images.

This invention will be further illustrated by the examples that follow:

Preparation of 1,2-Bis(dimethylphosphino)ethane bis-bisulfate, i.e. $DMPEH_2^{2+}.2HSO^-_4$ or $DMPE.2H_2SO_4$ Dissolve 470 mg of DMPE in 10 ml of ethanol in a 50 ml round-bottomed flask maintained under a nitrogen atmosphere. From a glass syringe, add, with stirring, 0.34 ml of concentrated sulfuric acid. After 10 minutes, filter the precipitate and recrystallize it from 10 ml. of methanol. Filter and dry under vacuum. 920 mg of a crystalline solid is obtained, which melts at 135°–136.5° C. Structure and purity of the compound was confirmed by its infra-red and nuclear magnetic resonance spectra and elemental analysis.

EXAMPLE 1 (100° C.)

Dissolve 1 g mannitol and 16.8 mg DMPE-bis(bisulfate) in about 35 ml low-oxygen distilled water, and adjust the pH of the solution to 2.0 with 3 N sulfuric acid. Under cover of nitrogen, and with stirring, add low-oxygen distilled water to a solution volume of 50 ml. Dispense 1 ml of this solution into each of several 10 cc vials. Freeze-dry in keeping with procedures well-known to those skilled in the art, stoppering under nitrogen. Reconstitute each vial with 1 ml of physiological saline containing about 10–20 mCi $^{99m}$Tc-pertechnetate. Labelling with $^{99m}$Tc-pertechnetate in 100° C. water bath for 30 minutes yielded less than 2% labelled product as analyzed by thin layer chromatography (TLC).

EXAMPLE 2 (133° C.)

Serval of the vials of Example 1 after reconstitution were labelled by placing them in an oil bath preheated and maintained at about 133° C. After 40 minutes of reaction time TLC analyses showed yields of 90–95% labelled product.

EXAMPLE 3

Dissolve 1 g mannitol, 150 mg sodium chloride, and 46 mg DMPE-bis(bisulfate) in 10 ml deoxygenated physiological saline solution (0.15 Molar). Adjust the pH of the solution to 1.4 by adding the required volume of 2 N hydrochloric acid. Dispense 1 ml of the solution into each of several 10 cc vials, flushing each with nitrogen gas for 20 seconds, closing with a teflon-coated stopper and crimp-sealing it.

Labelling Procedure I

Inject 50 mCi of $^{99m}$Tc-pertechnetate in 0.5 ml physiological saline into each of several vials and place them in an oil bath, preheated and maintained at 150°–155° C., for 5–10 minutes. HPLC analyses show yield of 90 to 100%.

Labelling Procedure II

Inject 50 mCi of $^{99m}$Tc-pertechnetate in 0.5 ml physiological saline into each of several vials and place them in a steam autoclave preheated to 100° C. Set the temperature control to 135° C., and when that temperature is achieved, maintain it for 20 minutes. Allow the system to cool to 100° C. and remove the vials. HPLC analyses show yields of 95 to 100%.

EXAMPLE 4

Dissolve 5 g mannitol and 230 mg DMPE-bis(bisulfate) in about 35 ml low-oxygen distilled water, and adjust the pH of the solution to 1.0 with 3 N sulfuric acid. Under cover of nitrogen, and with stirring, add low-oxygen distilled water gravimetrically, to a solution weight of 50 g. Dispense 1 ml of this solution into each of several 10 cc vials. Freeze-dry in keeping with procedures well-known to those skilled in the art, stoppering under nitrogen. Reconstitute each vial with 1 ml of physiological saline containing about 10–20 mCi $^{99m}$Tc-pertechnetate. Utilizing techniques similar to those of Example A above, autoclave for 30 minutes at 135° C. Thin layer chromatography (TLC) analyses show yields consistently greater than 95%.

EXAMPLE 5

Imaging of Rabbit Heart Using Tl-201 (Prior Art)

2 mCi of Thallium-201 (as thallous chloride in physiological saline containing 0.9% benzyl alcohol) is injected intravenously into a 2.5 Kg male New Zealand Albino rabbit. The rabbit is positioned under a Searle Pho-Gamma scintillation camera in such a way that the heart and lung area are covered by the field of view. Approximately 10 minutes after injection, sufficient counts are accumulated to produce an image of the heart analogous to that seen in clinical studies of humans.

EXAMPLE 6

Imaging of Rabbit Heart Using $^{99m}$Tc-labelled Products with ≧80% Yield of Desired Labelled Complex Greater than 1 mCi of the $^{99m}$Tc-labelled product of Example 2, 3 or 4 is injected into a rabbit and imaged as in Example 5. The quality and appearance of the heart image is similar to that obtained in Example 5.

EXAMPLE 7

Imaging of Baboon Heart Using $^{99m}$Tc-labelled Products with ≧80% of Desired Labelled Complex Greater than 10 mCi of the $^{99m}$Tc-labelled product of Example 2, 3 or 4 is injected intravenously into an adult baboon positioned under a scintillation camera as was the rabbit in Example 5. Excellent qulity images of the heart are obtained, which are equivalent to those characteristically obtained with TI-201 in humans.

EXAMPLE 8

Comparative Preparations of Dimethylphosphinoethane, Diethylphosphinoethane, and Dimethlphosphinopropane To 50 g physiological saline, which had been deoxygenated with flowing $N_2$, is added sufficient ligand [L] to have a concentration of $2.6 \times 10^{-3}$M (approx. 1 mg/ml saline), i.e. 57 μl dimethylphosphinoethane (DMPE), 74 μl diethylphosphinoethane (DEPE), or 55 μl dimethylphosphinopropane (DMPP). The resulting solution was acidified to a pH of about 2 with 3N $H_2SO_4$. After stirring under $N_2$ for five minutes, the solution was adjusted to pH=1.85±0.05 with 3N $H_2SO_4$ and 1.0 ml dispensed into $N_2$ purged 10 cc vials, which were then crimp sealed. 0.1 ml of $^{99m}TcO_4$-saline (approx. 20 mCi) was added to each vial. Vials were heated for either 30 minutes or 60 minutes at 100° C. in a vigorously boiling watei bath, or were heated 30 minutes at 135°±5° C. in a heated oil bath. TLC was used to analyze for the technetium complex-$TcL_2Cl_2^+$ and the results are shown in the table below:

| | % $TcL_2Cl_2^+$ Reaction Conditions | | |
|---|---|---|---|
| L | 100° C., 30 min. | 100° C., 60 min. | 135° C., 30 min. |
| DMPE | 14 | 14 | 97 |
| DEPE | 6 | 34 | 93 |
| DMPP | 14 | 61* | 92 |

*This value is partially an artifact due to poor resolution and/or side products. Actual yield is estimated to be ≦40%

This invention has been described in detail with particular reference to the preferred embodiments thereof. However, it will be appreciated that those skilled in the art, upon reading this disclosure, may make modifications and improvements within the spirit and scope of the invention.

I claim:

1. A method for preparing cationic lipophilic technetium complexes for radiodagnostic imaging, said method comprising (1) admising $^{99m}$Tc-pertechnetate with a target-seeking ligand or aqueous salt thereof, said ligand having the following structure:

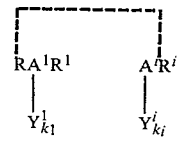

wherein:

i is an integer from 1 to 6;

R, $R^1$, $R^2$, $R^3$, $R^4$, $R^5$, and $R^6$ are each independently selected from hydrogen or substituted or unsubstituted alkyl, aryl, alkylaryl, arylalkyl, monocycloalkyl, polycycloalkyl, heterocyclic and carbocyclic groups, and R plus $R^i$ may be taken together to form a cyclic compound or separately to form a linear compound;

$Y^1$, $Y^2$, $Y^3$, $Y^4$, $Y^5$ and $Y^6$ are independently selected from hydrogen or substituted or unsubstituted alkyl, aryl, alkylaryl, arylalkyl, monocycloalkyl, polycycloalkyl, heterocyclic and carbocyclic groups;

$A^1$, $A^2$, $A^3$, $A^4$, $A^5$ and $A^6$ are each, independently, a donor atom having a free-electron pair available for complexing with Tc-99m or Tc-99 to form a cationic complex; and $k^1$, $k^2$, $k^3$, $k^4$, $k^5$ and $k^6$ are each independently zero or one; or

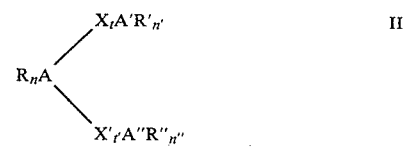

wherein:

R, R' and R" are independently selected from hydrogen or substituted or unsubstituted alkyl, aryl, alkylaryl, arylalkyl, monocylcloalkyl, polycycloalkyl, heterocyclic and carbocyclic groups;

X and X' are saturated or unsaturated alkyl groups; A, A' and A" are independently selected from the group of donor atoms having a pair of electrons available for complexing with Tc-99m or Tc-99 to form a cationic complex; t and t' are independently 0 or 1; n is 0, 1 or 2; and n' and n" are independently the integer 1 or 2; or

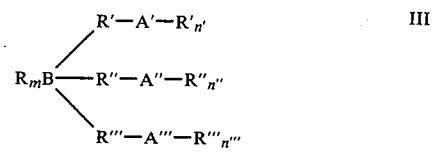

wherein

R, R', R" and R'" are independently selected from hydrogen or substituted or unsubstituted alkyl, aryl, alkylaryl, arylalkyl, monocycloalkyl, polycycloalkyl, heterocyclic and carbocyclic groups;

A', A" and A'" are independently selected from the group of donor atoms having a pair of electrons available for complexing with Tc-99m or Tc-99 to form a cationic complex;

B is an atom from the group of donor atoms having a pair of electrons available for complexing with Tc-99m or Tc-99, boron, or from the elements of Group IV A of the periodic table;

m is 0 or 1; and n, n', n" and n'" are independently the integer 1 or 2; and (2) heating the admixture to a temperature greater than 100° C. for a suitable length of time to complete the labelling reaction.

2. The method of claim 1 wherein each A is selected from the group consisting of P, As, N, O, S, Sb, Se and Te, thus obtaining a technetium-labelled radiodiagnostic agent.

3. The method of claim 1 wherein said temperature is in the range of about 130° C. to about 150° C.

4. The method of claim 1 wherein said target-seeking ligand has the formula:

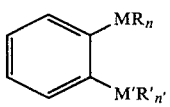

wherein M and M' are arsenic, phosphorus, nitrogen, sulfur, oxygen, selenium, tellurium, or any combination of them, n and n' are independently 1 or 2 depending upon the particular M and M', and R and R' are independently hydrogen, an alkyl group having from 1 to about 5 carbon atoms, or an aryl group.

5. The method of claim 1 wherein said target-seeking ligand has the formula:

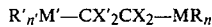

wherein M and M' are arsenic, phosphorus, nitrogen, sulfur, oxygen, selenium, tellurium, or any combination of them, n and n' are independently 1 or 2 depending on the particular M and M', R and R' are independently hydrogen, halide, an alkyl group having 1 to about 6 carbon atoms, or an aryl group.

6. The method of claim 1 wherein said target-seeking ligand has the formula:

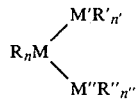

wherein M, M' and M" are independently selected from arsenic, phosphorous, nitrogen, sulfur, oxygen, selenium, and tellurium, n is 0 or 1 and n' and n" are independently 1 or 2 depending upon the particular M, M' and M" used, and R, R' and R" are independently selected from hydrogen, halide, an alkyl group having 1 to about 6 carbon atoms, or an aryl group.

7. The method of claim 1 wherein said target-seeking ligand has the formula:

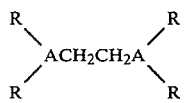

wherein A is P or As; and each R is independently H, a lower alkyl group having from 1 to about 6 carbon atoms, or phenyl.

8. The method of claim 1 wherein said target-seeking ligand has the formula:

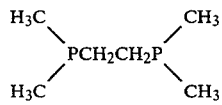

9. The method of claim 1 wherein said target-seeking ligand has the formula:

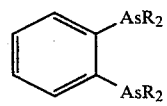

wherein R is H or a lower alkyl group having 1 to about 6 carbon atoms.

10. The method of claim 1 wherein said admixture is heated for a period of from about 5 to about 30 minutes.

11. The method of claim 1 wherein said admixture is heated to a temperature of about 150° C.

12. The method of claim 11 wherein said admixture is heated for a period of from about 5 to about 10 minutes.

13. The method of claim 1 wherein said admixture is heated to a temperature of at least 130° C.

14. The method of claim 1 wherein said target-seeking ligand is selected from the group consisting of dimethylphosphinoethane, diethylphosphinoethane, and dimethylphosphinopropane.

* * * * *